(12) United States Patent
Laakso et al.

(10) Patent No.: US 10,709,171 B2
(45) Date of Patent: Jul. 14, 2020

(54) CONTAINER FOR AN AEROSOL GENERATING DEVICE

(71) Applicant: JT International S.A., Geneva (CH)

(72) Inventors: Aki Laakso, Grantchester (GB); Kyle Adair, Lisburn (GB); Andrew Rogan, Forres (GB)

(73) Assignee: JT International S.A. (CH)

( * ) Notice: Subject to any disclaimer, the term of this patent is extended or adjusted under 35 U.S.C. 154(b) by 414 days.

(21) Appl. No.: 15/537,268

(22) PCT Filed: Nov. 24, 2015

(86) PCT No.: PCT/EP2015/077499
§ 371 (c)(1),
(2) Date: Jun. 16, 2017

(87) PCT Pub. No.: WO2016/096337
PCT Pub. Date: Jun. 23, 2016

(65) Prior Publication Data
US 2017/0347709 A1    Dec. 7, 2017

(30) Foreign Application Priority Data
Dec. 18, 2014    (EP) .................................. 14198925

(51) Int. Cl.
*A24F 47/00* (2020.01)
*A24F 15/18* (2006.01)

(52) U.S. Cl.
CPC ............ *A24F 47/008* (2013.01); *A24F 15/18* (2013.01); *A61M 2209/045* (2013.01)

(58) Field of Classification Search
None
See application file for complete search history.

(56) References Cited

U.S. PATENT DOCUMENTS

| | | | |
|---|---|---|---|
| 6,637,430 B1 * | 10/2003 | Voges | A61M 15/0065 128/200.14 |
| 8,757,169 B2 * | 6/2014 | Gysland | A24F 47/008 131/271 |
| 9,089,166 B1 * | 7/2015 | Scatterday | A24F 15/12 |
| 9,668,522 B2 * | 6/2017 | Memari | A24F 15/12 |
| 9,883,696 B2 * | 2/2018 | Liu | A24F 47/008 |
| 9,907,340 B2 * | 3/2018 | Liu | A24F 47/008 |

(Continued)

FOREIGN PATENT DOCUMENTS

| | | |
|---|---|---|
| KR | 101062248 B1 | 9/2011 |
| KR | 101094727 B1 | 12/2011 |

(Continued)

OTHER PUBLICATIONS

International Search Report for PCT/EP2015/077499 dated Jan. 27, 2016.

*Primary Examiner* — Thor S Campbell
(74) *Attorney, Agent, or Firm* — Lerner, David, Littenberg, Krumholz & Mentlik, LLP

(57) ABSTRACT

A container for an aerosol generating device comprises receiving means for receiving the aerosol generating device. One or more tanks are each arranged to retain a substance in use. For each tank, there is dispensing means for controllably transferring the substance from the tank to the aerosol generating device while the aerosol generating device is in the container.

14 Claims, 4 Drawing Sheets

(56) References Cited

U.S. PATENT DOCUMENTS

| | | | |
|---|---|---|---|
| 9,943,112 B2* | 4/2018 | Liu | A24F 47/008 |
| 10,081,531 B2* | 9/2018 | Murison | H05B 1/0227 |
| 2010/0242974 A1* | 9/2010 | Pan | A24F 47/008 |
| | | | 131/273 |
| 2011/0226236 A1* | 9/2011 | Buchberger | A61M 11/041 |
| | | | 128/200.23 |
| 2012/0167906 A1 | 7/2012 | Gysland | |
| 2012/0199663 A1* | 8/2012 | Qiu | A61M 11/041 |
| | | | 239/8 |
| 2013/0168880 A1 | 7/2013 | Duke | |
| 2013/0220316 A1 | 8/2013 | Oglesby et al. | |
| 2013/0306065 A1* | 11/2013 | Thorens | A24F 47/008 |
| | | | 128/202.21 |
| 2013/0319435 A1* | 12/2013 | Flick | A24F 47/008 |
| | | | 131/328 |
| 2013/0341218 A1* | 12/2013 | Liu | A24F 15/18 |
| | | | 206/242 |
| 2014/0123989 A1* | 5/2014 | LaMothe | A24F 47/008 |
| | | | 131/328 |
| 2014/0202454 A1 | 7/2014 | Buchberger | |
| 2014/0238396 A1 | 8/2014 | Buchberger | |
| 2014/0299137 A1* | 10/2014 | Kieckbusch | A24F 47/008 |
| | | | 131/328 |
| 2015/0053217 A1* | 2/2015 | Steingraber | A24F 47/008 |
| | | | 131/329 |
| 2015/0272216 A1* | 10/2015 | Dai | A61M 15/06 |
| | | | 131/328 |
| 2015/0282529 A1* | 10/2015 | Li | A24F 47/008 |
| | | | 131/273 |
| 2015/0305409 A1* | 10/2015 | Verleur | H02J 7/0022 |
| | | | 131/329 |
| 2015/0342258 A1* | 12/2015 | Chen | H05B 3/06 |
| | | | 131/329 |
| 2015/0359263 A1* | 12/2015 | Bellinger | H05B 1/0244 |
| | | | 392/394 |
| 2016/0219933 A1* | 8/2016 | Henry, Jr. | A24F 47/008 |
| 2016/0331036 A1* | 11/2016 | Cameron | H04M 1/7253 |
| 2017/0222468 A1* | 8/2017 | Schennum | A24F 47/008 |
| 2017/0334605 A1* | 11/2017 | Murphy | A24F 15/18 |

FOREIGN PATENT DOCUMENTS

| | | |
|---|---|---|
| WO | 2013102612 A2 | 7/2013 |
| WO | 2014066730 A1 | 5/2014 |

* cited by examiner

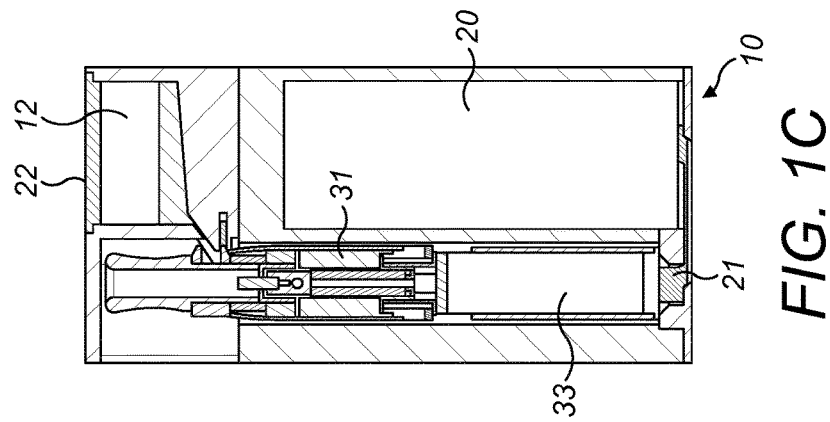
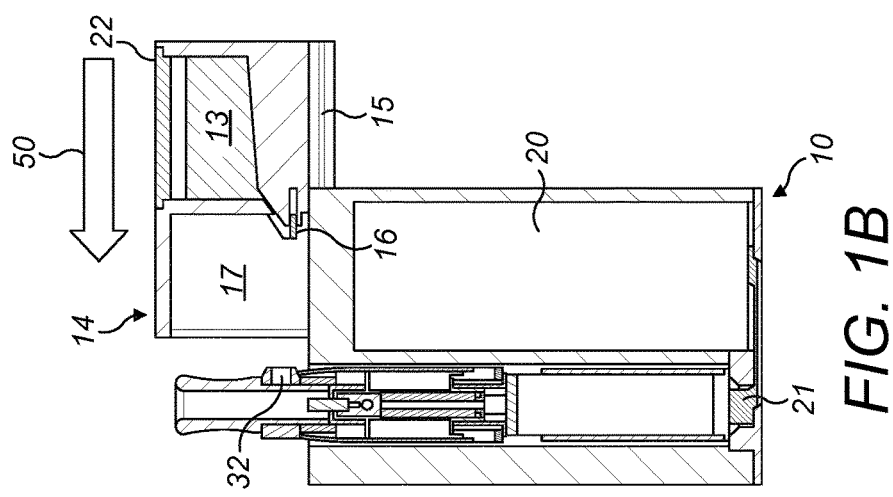
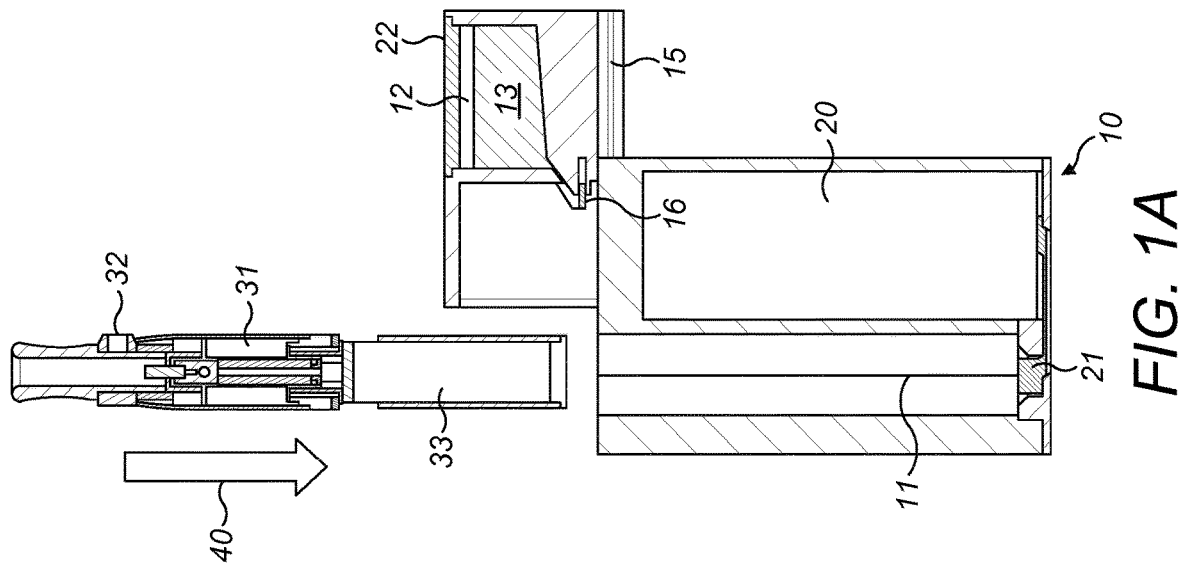

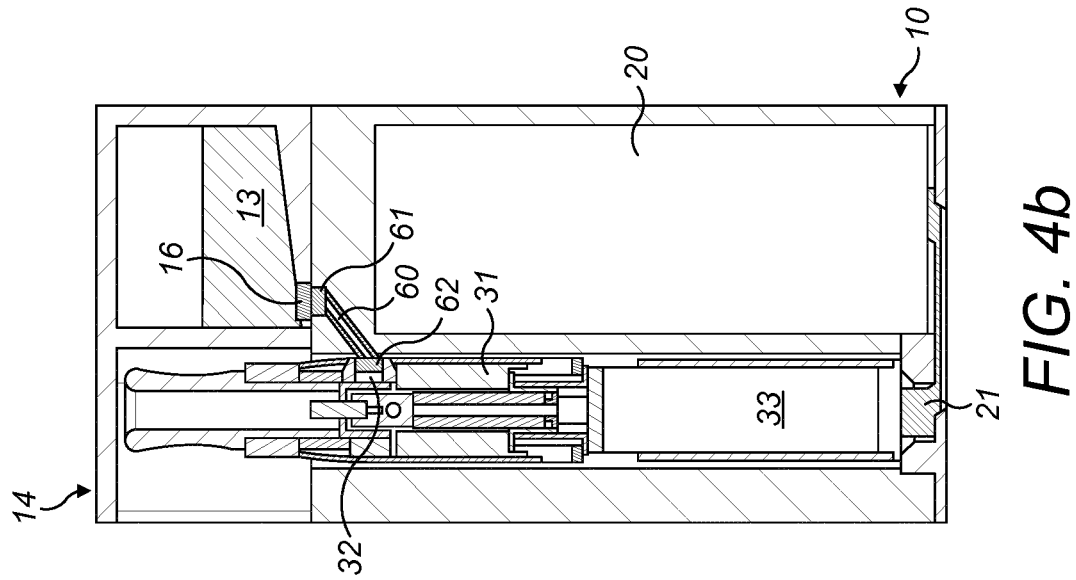
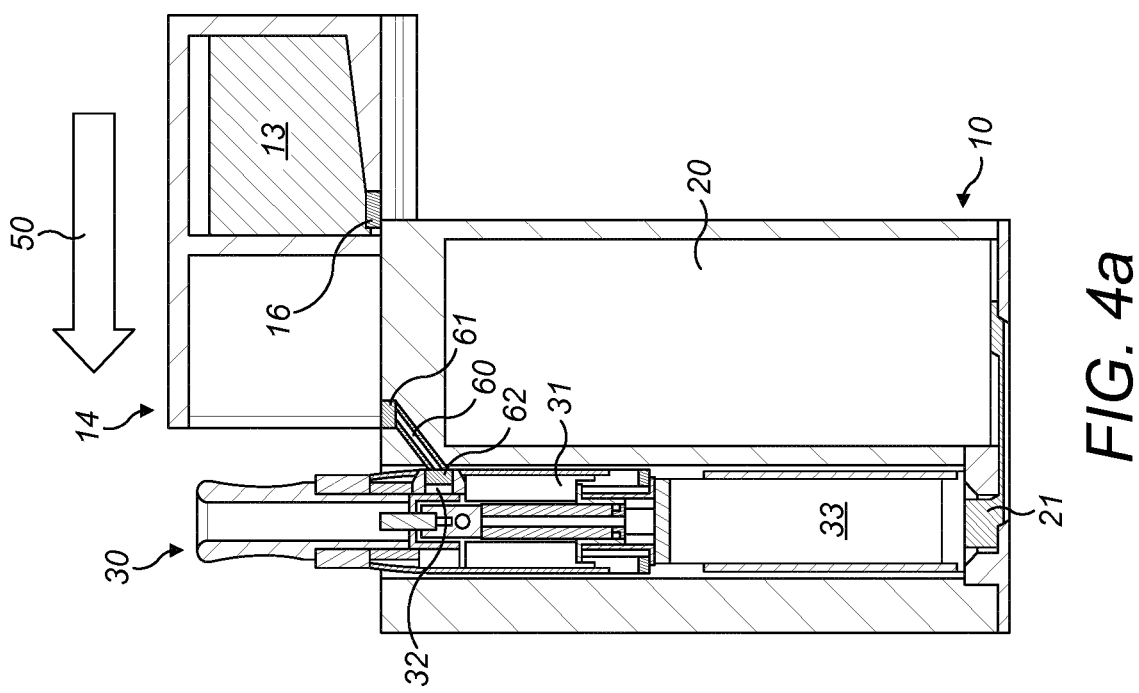

CONTAINER FOR AN AEROSOL GENERATING DEVICE

CROSS-REFERENCE TO RELATED APPLICATIONS

The present application is a national phase entry under 35 U.S.C. § 371 of International Application No. PCT/EP2015/077499, filed Nov. 24, 2015, published in English, which claims priority from EP 14198925.1, filed Dec. 18, 2014, the disclosures of which are incorporated herein by reference.

The present invention relates to a container for refilling an aerosol generating device such as an electronic cigarette.

Aerosol generating devices such as electronic cigarettes are relatively well known and are becoming increasingly popular. The most common operating principle for such electronic cigarettes is to provide a flavoured vapour to a user without burning material. They often comprise an electrically powered heat source and a reservoir of liquid, whereby the vapour is produced by delivering the liquid to the heat source.

Since the liquid is depleted during this process, after a certain amount of use the reservoir is emptied. Accordingly, some prior art electronic cigarettes provide a replaceable cartridge containing the heater and liquid reservoir which may be discarded and replaced when necessary. However such cartridges result in excessive waste since the heat source components are durable and far outlast the liquid. Other designs require the user to pour replacement liquid into the reservoir in order to replenish it. Given the small size of the components of these devices, such a process is not straightforward for the user and carries a risk of spillage. There is also a lack of precision related to manually refilling an electronic cigarette which results in a varied amount of liquid present in the reservoir after each refill. This may have an impact on the taste and therefore a detrimental effect on the user's experience.

Some prior art refilling devices use pressurised components and pumps to transfer a liquid into the reservoir. However, such complex components are often costly, difficult to assemble and susceptible to failure.

The present invention seeks to provide a user-friendly means for precisely refilling an electronic cigarette to overcome the problems of the prior art.

According to the present invention there is provided a container for refilling an aerosol generating device and an aerosol generating device adapted for use with the container. The container comprises a receiving means for receiving the aerosol generating device, one or more tanks, each arranged to retain a substance in use and, for each tank, dispensing means for controllably transferring the substance from the tank to the aerosol generating device while the aerosol generating device is in the container. The aerosol generating device comprises one or more internal reservoirs, each arranged to retain a substance in use and, for each internal reservoir, an inlet valve associated with the internal reservoir on an external surface of the aerosol generating device. The inlet valve is configured such that when it is connected with the dispensing means of the container, a substance may be transferred through the inlet valve into the associated internal reservoir.

With the container according to the present invention it is possible to provide a means to precisely refill an electronic cigarette which does not require any disassembly or handling of small parts and therefore is simple to operate for the user. Since the refilling is performed within a container, it further does not carry a risk of spilling the liquid or it coming into contact with the skin or internal electronic components of the aerosol generating device. The present invention also allows for automatic refilling while the aerosol generating device is stored, further improving the ease of use.

The container further provides the possibility of transferring a substance to the internal reservoir using gravity alone, eliminating the need for pressurised components and pumps. This provides an advantage in terms of the cost of components, the ease of assembly and the robustness of the container.

The container also provides means to store the aerosol generating device and protects against accidental damage to the delicate internal components for example from dropping.

One example of the present invention will now be described with reference to the accompanying drawings in which:

FIG. 1A-1C are schematic diagrams of the container and aerosol generating device of the present invention, illustrating the refilling procedure.

FIGS. 4A and 4B are schematic diagrams showing a further example of the present invention in which the liquid is transferred through a conduit in the container.

Figure 2A:
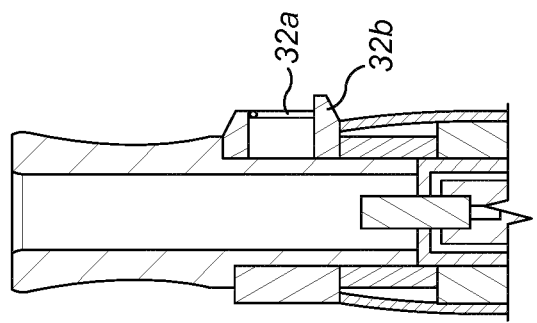
FIGS. 2A and 2B are schematic diagrams of the inlet valve of the aerosol generating device and outlet valve of the tank respectively.

Referring to FIG. 1A, a container 10 according to the invention comprises receiving means 11 for receiving an aerosol generating device such as an electronic cigarette 30 and a tank 12 to retain a substance such as an aerosol-generating liquid 13 for transferring to the internal reservoir 31 of the electronic cigarette 30.

In this example, the receiving means takes the form of a chamber 11 within the container 10, with an open end into which the electronic cigarette 30 may be inserted and a closed end on which it may rest. The length of chamber 11 is such that the electronic cigarette 30 sits substantially inside the container 10 when inserted and the cross section of the chamber 11 is similar to that of the electronic cigarette 30 so that it is housed securely. In this exemplary case the chamber length is slightly less than that of the electronic cigarette 30 so that the electronic cigarette 30 protrudes from the open container 10, improving the ease with which it may be removed.

The container 10 further comprises dispensing means to controllably transfer the aerosol-generating liquid 13 from the tank 12 to an internal reservoir 31 of the electronic cigarette 30. The internal reservoir 31 may be configured to contain at least 1 ml of liquid, more preferably 2 ml and even more preferably 3 ml of aerosol-producing substance. The dispensing means may comprise an outlet valve 16 associated with the tank 12 and an inlet valve 32 on the electronic cigarette 30. The outlet valve 16 and inlet valve 32 may be controllably connected to form a channel between the tank 12 and internal reservoir 31 of the electronic cigarette 30, through which the liquid 13 may be transferred.

Figure 2B:
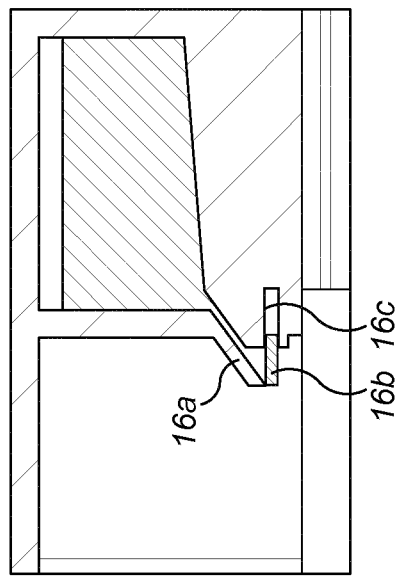
Figure 2C:
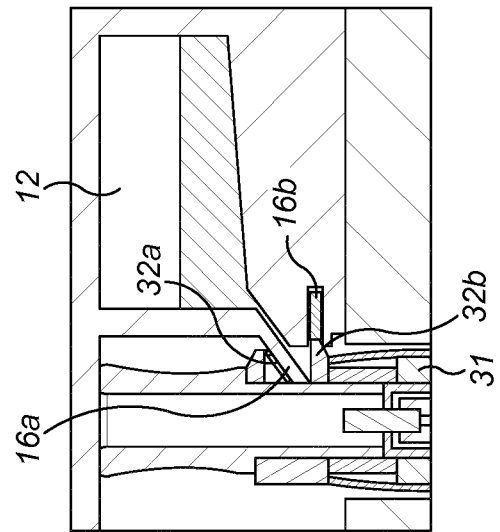
FIG. 2C shows the connected outlet and inlet valves which form a channel between the tank and aerosol generating device.

In this example this is achieved since the outlet 16 and inlet 32 valves have reciprocal opening mechanisms as shown in FIGS. 2A-2C, each configured to open the opposing valve when brought together with appropriate alignment and force. For example the inlet valve 32 of the electronic cigarette comprises an opening, blocked by a hinged closure flap 32a biased into a closed position and a protruding opening member 32b as shown in FIG. 2A. The outlet valve 16 associated with the tank 12 comprises a nozzle 16a containing a channel which is closed at its outer opening by closure tab 16b, as shown in FIG. 2B. The closure tab 16b is biased into a closed position by a spring within a recess 16c behind it. Upon bringing the valves together, as depicted in FIG. 2C, the nozzle 16a of the outlet valve fits within the opening of the inlet valve 32, opening the closure flap 32a whilst the protruding opening member 32b of the inlet valve presses the closure tab 16b of the outlet valve back into the recess 16c, opening a channel between the tank 12 to the internal reservoir 31 of the electronic cigarette 30.

In order to regulate the amount of liquid 13 transferred from the tank 12 to the internal reservoir 31, the electronic cigarette 30 or container 10 may contain means to stop the liquid being transferred upon the liquid within the internal reservoir reaching a predefined amount. In this example this takes the form of a float valve such as a ball which directly blocks the opening of the inlet valve 32 upon the liquid 13 in the reservoir 31 reaching a certain level or a mechanical connection to the closure flap 16b which is configured to close when the float valve is triggered. Alternatively, this function may be provided by a sensor disposed in the tank 12 which measures the amount of liquid remaining and provides a signal to the dispensing means to transfer the required amount of liquid 13 after which the valves are closed.

The container 10 of this example further comprises a cover portion 14 configured to move between an open position (FIGS. 1A and 1B), in which the electronic cigarette 30 protrudes from the container 10 and may be easily inserted and removed; and a closed position (FIG. 1C) in which it is secured. In this example, the movement of the cover portion 14 is provided by a slide mechanism 15 which restricts movement of the cover 14 to a direction perpendicular to that of the insertion direction as shown by arrow 50. In the present example, the tank 12 is disposed within the cover portion 14, occupying some of the internal volume. The cover portion further comprises a sub-compartment 17, open on the side adjacent to the inserted electronic cigarette 30 and arranged so as to substantially enclose the protruding section of the electronic cigarette 30 and secure it within the container 10 when the cover portion 14 is moved to the closed position.

To improve the functionality of the dispensing means it is also preferable for the chamber 11 to include means to restrict the orientation of the electronic cigarette 30 within the container 10 (not pictured) so that the inlet valve 32 of the electronic cigarette 30 is aligned with the outlet valve 16 of the tank 12 upon being connected. This may be achieved if the cross-sectional shape of the chamber 11 and electronic cigarette 30 has a limited order of rotational symmetry, for example an oval. In the case of an oval, assuming the electronic cigarette 30 is inserted with the correct end first, it may only take one of two orientations within the container 10. The inlet valve 32 may then be positioned on an external surface of the electronic cigarette 30 such that, in one of the two possible orientations within the container 10, the inlet valve 32 is aligned with the outlet valve 16 of the tank 12 upon being connected. The other orientation may be used as a means of storing the electronic cigarette 30 without refilling.

The orientation could be similarly restricted by the use of guide members. Such guide members may take the form of a protruding guide member on the outer surface of the electronic cigarette which is configured to be received by a longitudinal recess in the inner surface of the chamber 11, running in the direction of insertion 40 of the electronic cigarette 30.

The container 10 preferably further comprises a releasable retention mechanism (not shown), for example a clip mechanism, configured to hold the cover portion 14 in the closed position until released by a release means. The release means may comprise, for example, a release button mechanically connected to the retention mechanism or a grip allowing the user to exert sufficient force on the cover portion so that the retention means is released.

The container 10 may further comprise a battery 20 and associated electrical connections 21, marked in FIG. 1C, configured to recharge the battery 33 of the electronic cigarette 30 when it is inside the container 10. The container 10 then provides both refilling of the reservoir 31 and recharging of the battery 33 of the electronic cigarette 30 during storage. To further improve this function, the container 10 may further comprise means to determine the level of power remaining in the battery 33 such that recharging may occur only when required. The refilling and recharging processes may happen independently from each other so that refilling of the reservoir 31 of the electronic cigarette 30 may occur without recharging of the battery 33 and vice versa.

The container 10 may further comprise means to replenish the liquid 13 in the tank 12. In the example in which the tank 12 is disposed within the cover portion 14 this may be provided by using a replaceable cover portion which may be removed from the container 10 when emptied and replaced with a new cover portion in which the tank is full. Alternatively the container may have an opening access portion 21 which provides access to the tank 12. The tank 12 may then form a disposable component so that the access portion 21 may be opened and the tank 12 replaced when emptied.

In order to improve the functionality of the means to replenish the liquid 13 in the tank 12, the container 10 may further comprise a sensor (not pictured) disposed within the tank 12 to provide a reading of the amount of liquid 13 retained therein. The sensor would preferably be connected to a display on an external surface of the container 10 to provide information to the user on the amount of liquid 13 remaining in the tank 12 and signal when the tank needs to be replaced.

The refilling procedure of the electronic cigarette 30 using the exemplary container 10 will now be described in detail with reference to FIGS. 1A-1C.

The electronic cigarette 30 with reservoir 31 containing a volume of aerosol-generating liquid 13 depleted below the maximum level is inserted into the chamber 11 of the container 10 in direction 40 as shown in FIG. 1A. After insertion, the means to restrict the orientation of the electronic cigarette 30 in the container 10 ensures the inlet valve 32 of the electronic cigarette 30 is aligned with the outlet valve 16 of the tank 12 but separated by some distance in the direction of arrow 50. The user then applies a force to the outer face of the open cover portion on the far side from the electronic cigarette in the direction of closure 50 as shown in FIG. 1B. This action brings the outlet 16 and inlet 32 valves together, simultaneously connecting the valves and securing the device within the container with the cover closed, as illustrated in FIG. 1C.

As described above, the connected outlet and inlet valves form a channel between the tank 12 of the container 10 and the reservoir 31 of the electronic cigarette 30. Since, when in a similar orientation to that of FIGS. 1A-1C, the tank 12 is substantially above the connected outlet 16 and inlet 31 valves which are in turn substantially above the internal reservoir 31, transfer of the aerosol-generating liquid 13 from the container 10 to the electronic cigarette 30 will proceed under the action of gravity alone.

Transfer continues to be driven by gravity until the float valve releases the closure tab 16*b* to close the channel upon the liquid 13 within the reservoir 31 reaching a certain level. The outlet 16 and inlet 32 valves only allow passage of the liquid 13 in the direction described, thereby preventing the liquid 13 returning to the tank 12 if the container 10 is later rotated into a different orientation in which the tank 12 is below the inlet valve 32 of the electronic cigarette 30.

In this manner the liquid 13 in the internal reservoir 31 of the electronic cigarette 30 is replenished every time the electronic cigarette 30 is returned to the container 10 and the container is closed. Refilling by gravity in this way avoids the need for complex components such as pressurised tanks, which are more costly, more difficult to assemble and more susceptible to failure.

It will be appreciated that there are several alternative arrangements of the components of the container 10 which may be used instead of that of the exemplary arrangement described above to perform the same function. For example, the electronic cigarette 30 may have more than one reservoir 31, with the container 10 for the electronic cigarette 30 adapted to refill each of the reservoirs. An electronic cigarette 30 with two reservoirs for example has a number of advantages including an increased liquid-retaining volume, thereby extending the period of use before a refill is required. It also allows for filling with separate substances which may be mixed during vapourization. This is particularly advantageous for substances which are not miscible in liquid form and therefore cannot be stored in the same reservoir. It further allows for user-controlled mixing of components to customise the aerosol produced to the user's taste.

Figure 3B:
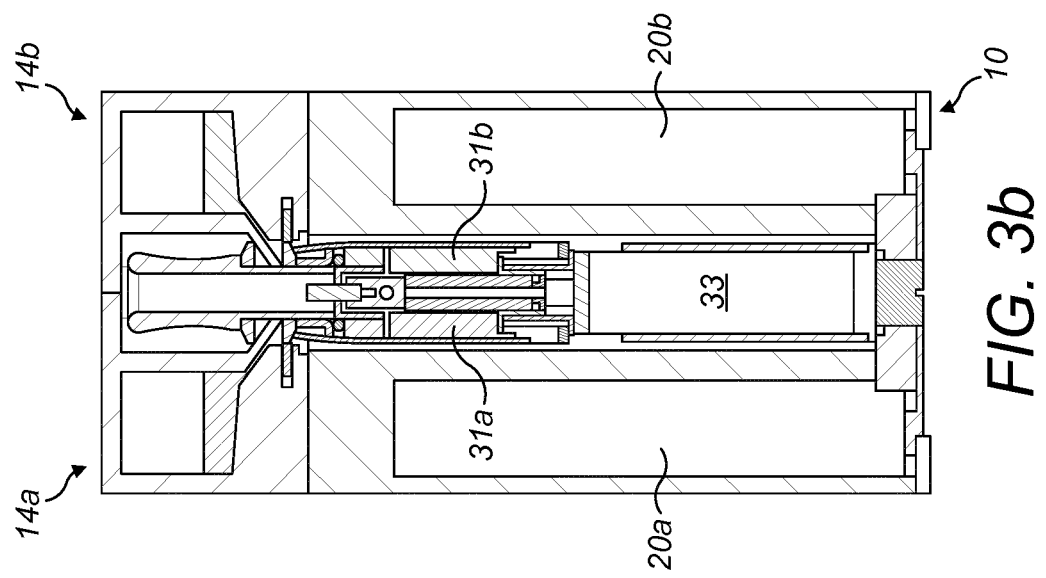
FIGS. 3A and 3B are schematic diagrams showing a further example of the present invention in which the aerosol generating device has two internal reservoirs which may be refilled with separate liquids stored in respective tanks in the container.
Figure 3A:
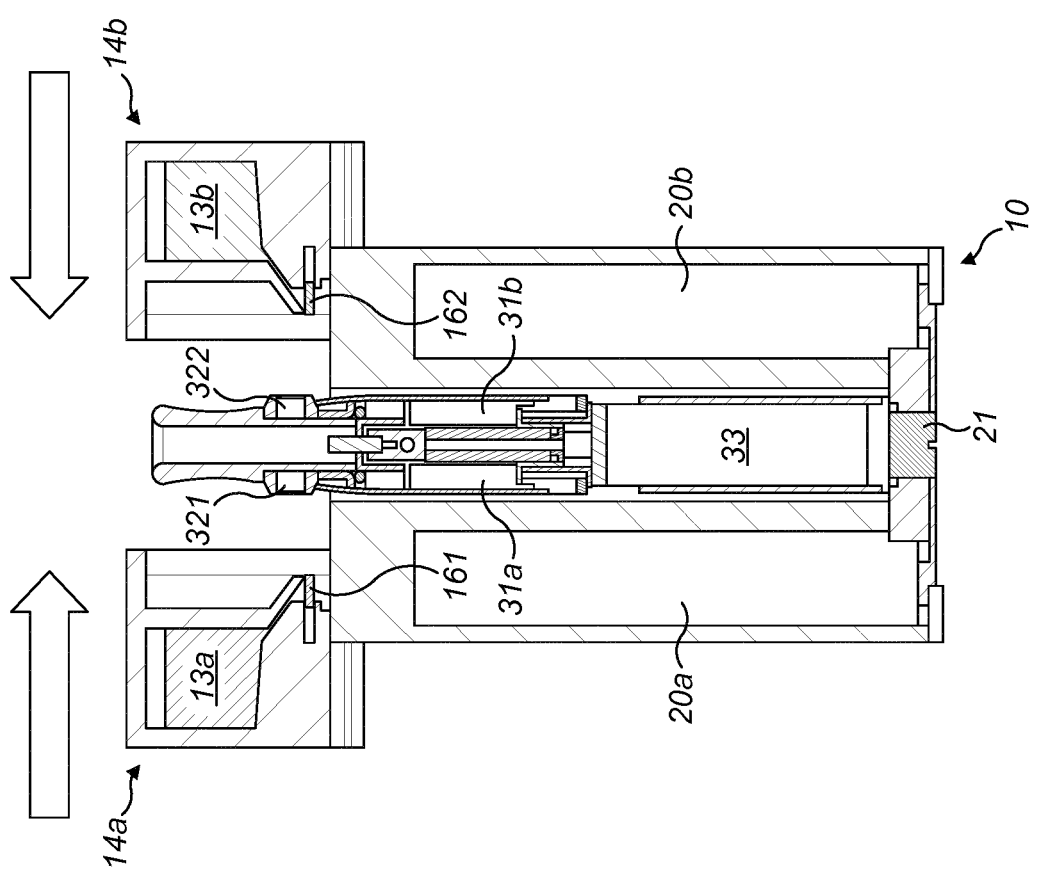

FIGS. 3A and 3B show an electronic cigarette 30 with two reservoirs 31*a*, 31*b*, each with an associated inlet valve, 321, 322, which allow for refilling of each reservoir with a different liquid. FIGS. 3A and 3B also show a container 10 adapted for refilling each of the reservoirs with a separate liquid. In this example, the cover portion is centrally divided into two parts, 14*a*, 14*b*, each with an internal tank configured to hold a separate liquid 13*a*, 13*b* and an outlet valve 161, 162 associated with each tank. The container is opened by moving each of the cover portion parts 14*a*, 14*b* to the open position, as shown in FIG. 3A, so that the electronic cigarette 30 may be inserted into the central chamber. The refilling procedure for each internal reservoir 31*a*, 31*b* is then as described above, with each cover part moved to the closed position, shown in FIG. 3B, so that the outlet valves 161, 162 are connected with the corresponding inlet valves 321, 322 on the outer surface of the electronic cigarette 30, opening the channels so that the liquid may pass from the tanks to the internal reservoirs under the action of gravity. In this manner, a separate liquid may be replenished in each reservoir of the electronic cigarette 30 while it is stored in the container 10.

In a further example the cover portion may form a separate component which is removably attached to the container 10 by a clip mechanism. In such an arrangement, the cover portion would be closed by bringing the cover portion 14 over the container 10 and electronic cigarette 30 therein and applying a downward force to clip the cover into place, securing the electronic cigarette within the container 10. This action would simultaneously secure the electronic cigarette within the container and connect the valves, allowing the liquid to be transferred from a tank 12 in the cover portion 14 to the internal reservoir 31 of the electronic cigarette 30.

In a further example, shown in FIGS. 4A and 4B, the container 10 may further comprise a conduit 60 running through the container 10 from a top opening on the upper surface of the container, adjacent to the cover, to a lower opening on an inner surface of the chamber 11, adjacent to the stored electronic cigarette 30. The top and bottom openings of the conduit may be closed with valves 61, 62, configured to open upon being engaged with the outlet valve 16 of the tank and inlet valve 32 of the electronic cigarette respectively. Therefore when the electronic cigarette 30 is inserted into the chamber 11 the inlet valve 32 is engaged with the lower conduit valve 62. Refilling of the electronic cigarette 30 may then be performed by moving the cover 14 to the closed position, shown in FIG. 4B, to engage the outlet valve 16 of the tank with the upper conduit valve 61. The outlet valve 16 of the tank 12 is then connected to the inlet valve 32 of the electronic cigarette 30 so that the substance may flow through the conduit 60 from the tank to the internal reservoir 31 of the electronic cigarette 30 under the action of gravity. As described above, the cover 14 may alternatively form a removable component which is attached via a clip mechanism. In this case, by bringing the cover over the electronic cigarette 30 within the case and clipping it into place, the outlet valve 16 of the tank is connected with the upper valve 61 of the conduit 60 allowing the liquid to be transferred from the tank 12 to the internal reservoir 31 of the electronic cigarette 30. These arrangements allow for a greater proportion of internal volume of the cover 14 to be occupied by the tank 12 thereby allowing a greater volume of liquid to be stored.

In a further arrangement, the connecting of the valves may be mechanically controlled by an external control button or by a remote control device such as a mobile phone or computer rather than closure of the container, such that the user may decide when refilling should be performed. The remote control device may be configured to estimate the content of the reservoir in the electronic cigarette and refill the internal reservoir 31 accordingly.

In a further arrangement, the connecting of the valves may be electronically controlled by internal software stored on a chip within the container 10, which may use information provided by sensors in the tank 12 and internal reservoir 31 to monitor the amount of liquid stored therein and drive the opening and the closure of the corresponding valves accordingly to transfer the required amount of liquid from the tank 12 to the electronic cigarette 30. This arrangement may be extended by the inclusion of means to communicate with a mobile phone with dedicated software also able to drive the process of refilling or the analysis of the liquid content. For example, the software may be configured to send an SMS to the user when the substance in the tank 12 is almost depleted and simultaneously order replacement liquid from the supplier's website. It could further provide information on the address of the closest supplier and when the order is ready to be collected.

The examples of the present invention described provide a container 10 for an aerosol generating device 30 which enables the refilling of the aerosol generating device with a precise amount of aerosol-generating substance in a user-friendly manner without any disassembly or handling of small parts, in contrast to many prior art devices. Furthermore, refilling is performed within the container and therefore carries a reduced risk of spillage of the refill substance.

The user experience is further improved by the possibility of automatic refilling while the aerosol generating device is stored within the container whilst the container further offers protection against accidental damage of the aerosol generating device. Finally, the possibility of transferring the substance using gravity alone rather than by pressurised components and pumps provides advantages in terms of the cost of components, the ease of assembly and the robustness of the device.

The invention claimed is:

1. A container for an aerosol generating device, the container comprising:

receiving means for receiving the aerosol generating device;

one or more tanks each arranged to retain a substance in use;

for each tank, dispensing means for controllably transferring the substance from the tank to the aerosol generating device while the aerosol generating device is in the container; and a cover portion configured to move between an open position in which a device may be received in and removed from the container, and a closed position in which the aerosol generating device is retained within the container, wherein the tank retaining the substance is disposed within the cover portion.

2. A container for an aerosol generating device, the container comprising:

receiving means for receiving the aerosol generating device;

one or more tanks each arranged to retain a substance in use; and for each tank, dispensing means for controllably transferring the substance from the tank to the aerosol generating device while the aerosol generating device is in the container, wherein the dispensing means comprises:

an outlet valve associated with the tank; and connecting means for connecting the outlet valve with an inlet valve on the aerosol generating device; arranged such that, in use, the connected outlet and inlet valves form a channel through which the substance may be transferred from the tank to the aerosol generating device by the action of gravity.

3. The container of claim 2 further comprising a cover portion configured to move between:

an open position in which a device may be received in and removed from the container; and a closed position in which the aerosol generating device is retained within the container.

4. The container of claim 3, configured such that the substance is transferred when the cover portion is closed and the aerosol generating device is retained within the container.

5. The container of claim 4, wherein the means for connecting the outlet valve with the inlet valve is operated by movement of the cover to the closed position while the aerosol generating device is in the container.

6. The container of claim 3, further comprising a slide mechanism to provide the movement between the open and closed position.

7. The container of claim 2, further comprising means to restrict the orientation of the aerosol generating device within the container to ensure the inlet valve of the device is aligned with the outlet valve of the tank when connected.

8. The container of claim 7 wherein the means to restrict the orientation of the aerosol generating device is provided by the receiving means, comprising:

a chamber wherein the size and shape of the chamber is substantially similar to that of the aerosol generating device such that it closely fits within the chamber; and the cross sectional shape is such that the orientation of the aerosol generating device is restricted within the chamber.

9. The container of claim 2, further comprising a battery to supply power to at least one of the aerosol generating device and the dispensing means.

10. An aerosol generating device for use with the container of claim 2, the aerosol generating device comprising:

one or more internal reservoirs, each arranged to retain a substance in use; and for each internal reservoir, an inlet valve associated with the internal reservoir on an external surface of the aerosol generating device; wherein the inlet valve is configured such that, when it is connected with a dispensing means of the container, a substance may be transferred though the inlet valve into the associated internal reservoir.

11. The aerosol generating device of claim 10 further comprising:

a power source;

a heater assembly;

a heater control means for selectively supplying power from the power source to the heater assembly; and a substance transfer means for controllably drawing the substance from the one or more internal reservoirs to the heater assembly; such that, when power is supplied to the heater assembly together with the substance, an aerosol is generated.

12. The aerosol generating device of claim 11 arranged such that, when the inlet valve lies substantially above the associated reservoir, filling of the reservoir will proceed under the action of gravity when the inlet valve is connected with the dispensing means of the container.

13. The aerosol generating device of claim 11, wherein the one or more internal reservoirs is configured to contain at least 1 ml of liquid of aerosol-producing substance.

14. The container of claim 2, wherein the container is configured such that in use with the aerosol generating device, each of the one or more tanks is disposed above a corresponding reservoir of the aerosol generating device, such that the container is configured to transfer the substance from each of the one or more tanks to the corresponding reservoir solely by the action of gravity.

* * * * *